United States Patent [19]
Henkelmann et al.

[11] Patent Number: 5,196,611
[45] Date of Patent: Mar. 23, 1993

[54] PREPARATION OF ALKYL, ALKENYL, AND ALKYNYL CHLORIDES

[75] Inventors: Jochem Henkelmann, Ludwigshafen; Irene Troetsch-Schaller, Frankenthal; Thomas Wettling, Limburgerhof; Thomas-Michael Kahl, Roemerberg; Leopold Hupfer, Friedelsheim; Wolfgang Franzischka, Frankenthal; Hermann Koehler, Bobenheim, all of Fed. Rep. of Germany

[73] Assignee: BASF Aktiengesellschaft, Ludwigshafen, Fed. Rep. of Germany

[21] Appl. No.: 879,214

[22] Filed: May 6, 1992

[30] Foreign Application Priority Data

May 18, 1991 [DE] Fed. Rep. of Germany ....... 4116365

[51] Int. Cl.$^5$ .................. C07C 17/16; C07C 41/18

[52] U.S. Cl. .................... 568/663; 570/261; 570/217; 568/681; 568/686; 536/18.4; 536/18.5; 536/122

[58] Field of Search .......... 568/663, 681, 686; 570/261, 217; 536/18.4, 18.5, 122

[56] References Cited

U.S. PATENT DOCUMENTS 4,783,526 11/1988 Obrian et al. ............... 536/18.5

Primary Examiner—Howard T. Mars
Attorney, Agent, or Firm—Keil & Weinkauf

[57] ABSTRACT

The preparation of an alkyl, alkenyl, or alkynyl chloride by the reaction of a corresponding alcohol with phosgene or thionyl chloride in the presence of a phosphine oxide acting as catalyst, wherein the catalyst used is an aliphatic, cycloaliphatic, or cyclic/aliphatic phosphine oxide.

1 Claim, No Drawings

PREPARATION OF ALKYL, ALKENYL, AND ALKYNYL CHLORIDES

The present invention relates to a novel process for the preparation of alkyl, alkenyl, and alkynyl chlorides by the reaction of corresponding alcohols with phosgene or thionyl chloride in the presence of a phosphine oxide acting as catalyst.

The said alkyl, alkenyl, and alkynyl chlorides are known per se and are useful as intermediates for various organic syntheses.

GB-A 2,182,039 discloses the chlorination of alcohols using phosgene or thionyl chloride in the presence of triarylphosphine oxides or triarylphosphine sulfides. This method is unsatisfactory, however, since it is necessary to use the triarylphosphine oxides in stoichiometric excess on account of their poor reactivity, and their low degree of solubility impedes the process of working up the reaction mixture.

It is thus an object of the invention to overcome these drawbacks.

Accordingly, we have found a novel process for the preparation of an alkyl, alkenyl, or alkynyl chloride by the reaction of a corresponding alcohol with phosgene or thionyl chloride in the presence of a phosphine oxide acting as catalyst, wherein the catalyst used is an aliphatic, cycloaliphatic, or cyclic/aliphatic phosphine oxide.

The process of the invention can be represented by the following equation:

$$R-OH + COCl_2 \xrightarrow{R_3PO} R-Cl + CO_2 + HCl$$
$$(or\ SOCl_2) \qquad\qquad\qquad (or\ SO_2)$$

The catalyst to be used in accordance with the present invention is an aliphatic, cycloaliphatic, or cyclic/aliphatic phosphine oxide.

Preferred catalysts are trialkylphosphine oxides having a $C_1$–$C_{12}$-alkyl moiety and in particular a $C_4$–$C_8$-alkyl moiety, particularly preferred examples thereof being tributyl-, trihexyl-, and trioctyl-phosphine oxides.

We particularly prefer to use a mixture of trihexyl-, dihexyloctyl-, hexyldioctyl-, and trioctyl-phosphine oxides.

Preferred cycloaliphatic phosphine oxides are tricycloalkylphosphine oxides having a $C_3$–$C_{12}$-cycloalkyl moiety and especially a $C_5$- or $C_6$-cycloalkyl moiety, a particular example being tricyclohexylphosphine oxide.

Other suitable catalyst are aliphatic bisphosphine oxides and cyclic/aliphatic phosphine oxides of the general formulae

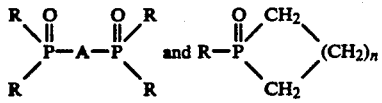

in which A denotes an alkylene group containing from 2 to 6, and preferably from 4 to 6, and more preferably 4, bridging members, and the radicals R are $C_1$–$C_{12}$-alkyl groups, preferably $C_1$–$C_4$-alkyl groups, such as, in particular, methyl and ethyl, or $C_3$–$C_{12}$-cycloalkyl groups, preferably $C_5$-and $C_6$-cycloalkyl groups, such as, in particular, cyclohexyl. The index n is preferably an integer from 2 to 4, especially 3.

The said aliphatic, cycloaliphatic, or cyclic/aliphatic phosphine oxides are preferably used in an amount of from 0.001 to 0.1 mole and more preferably in an amount of from 0.005 to 0.05 mole per mole of alcoholic hydroxyl groups.

Particularly suitable alcohols to be used in the process of the invention are those having the formula

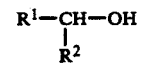

in which $R^1$ and $R^2$ stand for hydrogen, alkyl, alkenyl, alkynyl, alkoxy, aryloxy, hydroxyalkyl, hydroxyalkenyl or hydroxyalkynyl.

Taking into consideration the desired end products, the meanings of $R^1$ and $R^2$ in the above definition of said alcohols are preferably as follows:

hydrogen, $C_1$–$C_{22}$-alkyl, preferably $C_4$–$C_{18}$-alkyl and more preferably $C_6$–$C_{10}$-alkyl, such as, in particular, n-hexyl and n-octyl;

$C_3$–$C_{22}$-alkenyl, preferably $C_4$–$C_6$-alkenyl, such as, in particular, butenyl;

$C_3$–$C_{22}$-alkynyl, preferably $C_3$–$C_8$-alkynyl, such as, in particular, propynyl;

$C_1$–$C_{22}$-alkoxy, preferably $C_1$–$C_4$-alkoxy, such as, in particular, propoxy;

mono- or bi-nuclear aryloxy such as, in particular, phenyloxy, in which the aromatic rings may contain hetero atoms such as oxygen, sulfur, or nitrogen and/or may be substituted by up to three $C_1$–$C_{12}$-alkyl groups, halogen atoms such as fluorine, chlorine, and bromine, or $C_1$–$C_4$-alkoxy groups;

$C_1$–$C_{16}$-hydroxyalkyl, preferably $C_2$–$C_{12}$-hydroxyalkyl and more preferably $C_4$–$C_8$-hydroxyalkyl, such as, in particular, hydroxybutyl, hydroxyhexyl, and hydroxyoctyl;

$C_1$–$C_{16}$-hydroxyalkenyl, preferably $C_2$–$C_{12}$-hydroxyalkenyl and more preferably $C_4$–$C_8$-hydroxyalkenyl, such as, in particular, hydroxybutenyl, hydroxyhexenyl, and hydroxyoctenyl;

$C_1$–$C_{16}$-hydroxyalkynyl, preferably $C_2$–$C_{12}$-hydroxyalkynyl and more preferably $C_4$–$C_8$-hydroxyalkynyl, such as, in particular, hydroxybutynyl, hydroxyhexynyl, and hydroxyoctynyl.

Such radicals, except for hydrogen, may themselves carry substituents, preferably $C_1$–$C_4$-alkyl, $C_1$–$C_4$-esters, cyano, halogen such as, in particular, fluorine, chlorine, and bromine, aryl such as, in particular, phenyl and 4-methoxyphenyl, and aryloxy such as, in particular, phenyloxy.

Preferred alcohols are:
2-(4-methoxyphenyl)ethan-1-ol
2-ethylhexan-1-ol
n-octan-1-ol
3-buten-1-ol
propynol
butane-1,4-diol
octane-1,8-diol.

Taking into consideration the desired end products, we particularly prefer to use hexane-1,6-diol.

Other suitable alcohols are those derived from sugars, for example 2,3,6,3',4'-penta-O-acetylsucrose.

The alcohols are reacted with thionyl chloride or, preferably, with phosgene. The molar ratio of thionyl chloride or phosgene to alcohol is advantageously from 1 to 1.5 moles and preferably from 1.1 to 1.2 moles of chlorinating agent per mole of alcoholic hydroxyl groups.

The reaction is generally carried out at a temperature of from 40° to 120° C. and preferably from 70° to 90° C.

The reaction is advantageously carried out at atmospheric pressure, but reduced or elevated pressures may be used, for example pressures ranging from about 0.8 to 5 bar.

The reaction time is normally from 1 to 6 hours and is usually from 2 to 3 hours.

It may be advantageous to carry out the reaction in a solvent. Suitable solvents are alkyl esters such as ethyl acetate and methyl adipate, aryl esters such as methyl benzoate, and aromatic chlorine compounds such as dichlorobenzene. Preferred solvents are aromatic hydrocarbons such as toluene, xylene, and cumene.

The amount of solvent used is normally from one to ten times and preferably from two to five times greater than that of the alcohol.

The reaction may be carried out batchwise or continuously, but a batch operation is to be preferred.

It is preferred to use a phosphine oxide which is liquid at the reaction temperature and can be metered in the liquid state. Thus phosphine oxides which are liquid at room temperature are particularly useful from an engineering aspect.

The end product is isolated from the reaction mixture by known methods, generally by distillation, if desired after removal of any excess phosgene or thionyl chloride.

The distillation residues containing catalyst may be recycled to the reaction.

The alkyl, alkenyl, and alkynyl chlorides produced in economical yields by the process of the invention are known to be valuable intermediates for organic syntheses, particularly for the synthesis of plant protectants, galvanizing auxiliaries, and plastics precursors.

EXAMPLES

Example 1

Preparation of 2-(4-methoxyphenyl)ethyl chloride 11 g (0.11 mole) of phosgene were added to 4.4 g (0.02 mole) of tri-n-butylphosphine oxide during the course of 15 minutes at a temperature of 80° C. The temperature was then held at 90°-100° C. while 108 g (1.09 moles) of phosgene and 152 g (1.00 mole) of 2-(4-methoxyphenyl)ethanol were added over 1 hour. To complete the reaction, the mixture was kept at this temperature for another hour.

Excess phosgene was then removed from the product by bubbling nitrogen through the mixture for from 2 to 3 hours at a temperature of 90° C.

Subsequent distillation at 127°-130° C./20 mbar gave the 2-(4-methoxyphenyl)ethyl chloride in a yield of from 95 to 99% and a purity of 99.6%.

Example 2

Preparation of 1,6-dichlorohexane.

In a manner similar to that described in Example 1, 11 g (0.11 mole) of phosgene were added to 6.8 g (0.018 mole) of trioctylphosphine oxide. A further 69 g (0.7 mole) of phosgene plus 42 g (0.36 mole) of hexane-1,6-diole were then added over a period of 2 hours at a temperature of from 84° to 91° C., after which the reaction was completed by keeping the reaction mixture at 88° C. for one hour.

Removal of the excess phosgene and subsequent distillation at 100° C./30 mbar gave 1,6-dichlorohexane in a yield of 95% and a purity of 99.5%.

Example 3

Preparation of 1,4-dichlorobutane

In a manner similar to that described in Example 1, 19.7 g (0.2 mole) of phosgene were added to 18.6 g (0.085 mole) of tributylphosphine oxide. A further 350.4 g (3.55 moles) of phosgene plus 153.2 g (1.7 moles) of butane-1,4-diole were then added. Subsequent distillation at 50° C./100 mbar gave the 1,4-dichlorobutane in a yield of 95% and a purity of 99.5%.

We claim:

1. A process for the preparation of an alkyl, alkenyl, or alkynyl chloride by the reaction of a corresponding alcohol with phosgene or thionyl chloride in the presence of a phosphine oxide acting as catalyst, wherein the catalyst used is an aliphatic, cycloaliphatic, or cyclic/aliphatic phosphine oxide.

* * * * *